(12) United States Patent
Howard, Jr. et al.

(10) Patent No.: US 10,306,884 B1
(45) Date of Patent: Jun. 4, 2019

(54) ORGANOSILANE-BASED MULTI-PURPOSE CLEANING COMPOSITIONS AND METHODS

(71) Applicants: James Joseph Howard, Jr., Parkland, FL (US); Tyler Howard, Parkland, FL (US)

(72) Inventors: James Joseph Howard, Jr., Parkland, FL (US); Tyler Howard, Parkland, FL (US)

(*) Notice: Subject to any disclaimer, the term of this patent is extended or adjusted under 35 U.S.C. 154(b) by 166 days.

(21) Appl. No.: 15/613,260

(22) Filed: Jun. 4, 2017

Related U.S. Application Data

(60) Provisional application No. 62/345,748, filed on Jun. 4, 2016.

(51) Int. Cl.
| | |
|---|---|
| *A01N 33/12* | (2006.01) |
| *C08K 5/00* | (2006.01) |
| *A01N 25/02* | (2006.01) |
| *A01N 25/30* | (2006.01) |
| *A01N 55/00* | (2006.01) |
| *A01N 59/00* | (2006.01) |

(52) U.S. Cl.
CPC ............. *A01N 33/12* (2013.01); *A01N 25/02* (2013.01); *A01N 25/30* (2013.01); *A01N 55/00* (2013.01); *A01N 59/00* (2013.01); *C08K 5/0058* (2013.01); *A01N 2300/00* (2013.01)

(58) Field of Classification Search
CPC .............. C11D 3/162; C11D 9/36; C11D 9/44
See application file for complete search history.

(56) References Cited

U.S. PATENT DOCUMENTS

| | | | |
|---|---|---|---|
| 7,662,433 B2* | 2/2010 | Ford | B29D 11/00865 427/163.1 |
| 9,103,969 B2* | 8/2015 | Biteau | G02B 1/105 |
| 9,133,348 B2* | 9/2015 | Feret | C08G 65/336 |
| 2015/0355387 A1* | 12/2015 | Hazle | C08K 5/0075 351/159.57 |

* cited by examiner

*Primary Examiner* — Charles I Boyer
(74) *Attorney, Agent, or Firm* — Diana Mederos; Mederos Legal, PLLC

(57) ABSTRACT

Multi-purpose cleaning compositions and methods of manufacture and application thereof. The multipurpose cleaning compositions comprise a mixture of an aqueous solution of an organosilane. The solution may also contain surfactants and fragrance from natural and artificial sources. The multi-purpose cleaning solutions are sprayed on any surface, allowed to cure, and result in long-lasting cleaning effects such as odor reduction, pest repellency, antifouling, antibacterial, biocidal, and surface resilience. The cleaning compositions have a long shelf life and resistance to thermal degradation.

19 Claims, No Drawings

ORGANOSILANE-BASED MULTI-PURPOSE CLEANING COMPOSITIONS AND METHODS

CROSS-REFERENCE TO RELATED APPLICATION

This application claims the benefit of U.S. provisional application No. 62/345,748, filed Jun. 4, 2016, the contents of which are hereby incorporated by reference.

FIELD OF THE DISCLOSURE

The present disclosure relates to multi-purpose cleaning compositions and methods of making and using thereof. The present disclosure pertains to aqueous compositions for general cleaning, protectant, and odor reducing purposes. More specifically, the present disclosure presents multi-purpose cleaning compositions containing at least one organosilicon compound in a water-based solution.

BACKGROUND

Microbial growth is a nuisance in various industries as well as in regard to consumer goods and around the home. Cleaning products are popular temporary solutions to reducing microbial growth, eliminating odors caused by biofouling and microbial growth, and preventing the spread of pathogens. For example, a solid surface in a school, hospital, or home is traditionally wiped down with a solution containing an antibacterial or biocide. However, these surfaces need continuous re-application and do not prevent cell adhesion and biofilm formation. Microbial resistance is still a problem. Also, traditional cleaning products do not have lasting effects on non-solid and dry surfaces or substrates.

Presently, management and reduction of odors on an industrial scale is difficult to manage. Namely, the solid waste, municipal solid waste, and mixed waste industries are required to minimize the prevalence of bad odors coming from waste in an environmentally friendly manner. Most odors are compounds released into the air from a solid surface, sludge, or liquid. Some of the troublesome odors from garbage, compost, and sewer sludge include ammonium compounds, mercaptans, sulfides, indoles, skatoles, and thiocresols.

The most common odor eliminators or odor reducers used are based on alcohol, corn husk and corn derivatives, probiotics, or masking fragrances. The problem with these common odor eliminators is that they do not last long enough, often requiring constant application through a misting system. Furthermore, such traditionally used odor reducer or eliminators are temporarily effective at reducing or eliminating the airborne odor particles, including smoke and smog, but are not effective at treating the odor source to prevent or reduce the release of the airborne odor particles for an extended period of time.

Antifouling and anti-biofouling compositions prevent the growth of organisms on or in a medium. Biocidal compositions destroy, deter, render harmless, or control populations of pathogens and pests. Biocides have also been used to reduce odors caused by pathogens, but the biocides traditionally used are inefficient in large-scale applications for persistent odors. In such cases, odor elimination is temporary, and multiple repeat applications are required.

Antifouling compositions have been integrated into paints, films, and lacquers and then applied to a solid surface that is exposed to moisture, such as a shup's hull. The antifouling composition serves to prevent the attachment and proliferation of bivalves such as mussels and crustaceans such as barnacles.

Antifouling coatings have also traditionally been applied to protect surfaces from fouling due to other pests and water-related damage in general. Traditional antifouling coatings contain copper or tin which leach out into the surrounding environment and can potentially harm non pests or bio accumulate and cause teratogenic effects or disrupt hormones. For example, paints and lacquers for ship hulls contain copper or tin to prevent arthropods in general, barnacles, mollusks, bryozoans, amphipods, annelids, hydroids, algae, and slime mold from attaching to the ship or boat and corroding the boat's surface. The copper and tin is known to leach out of the paint or lacquer, especially under acidic conditions, and into the water, exposing non-targeted organisms to the toxic copper and tin and causing bioaccumulation and biomagnification.

Some antifouling and biocidal compositions are used in ballast water to aid in the prevention of transmission of invasive species. Current compositions are not effective and lead to resistance because the currently used compositions degrade too quickly and do not repel or deter invasive species or other pests. Therefore, when a sea vessel such as a barge travels from Asia to North America, there will likely still be invasive and destructive zebra mussels alive that will proliferate, cause physical damage, and kill off native mollusks in the zebra mussels' non-native environment.

It is well-documented that organosilicon compounds such as quaternary ammonium organosilanes that contain hydrolyzable groups are a popular choice as a biocidal and/or antibacterial ingredient in antifouling and biocidal compositions. It is believed that the cationic quaternary ammonium group of an organosilicon quaternary ammonium antimicrobial agent can form an associative bond with a variety of surfaces and is relatively environmentally friendly.

Organosilanes are typically used in products as a coupling agent to aid in boding organic polymers to inorganic materials such as plastics and metals. Organosilanes undergo hydrolysis reactions that result in the condensation and bonding of the organosilane to an inorganic surface. When applied to a surface, hydrolysis and condensation reactions of the silane take place. The bond between the silicon atom and the oxygen hydrolyze in an aqueous solution or environment. The hydrolysis results in reactive silanol, a silicon bonded to a hydroxyl group. Then the reactive silanol condenses with other reactive silanols to form a siloxane polymer with silicon-oxygen bonds that are stable. The resulting polymer couples with the molecules of the surface to which it is applied, adhering as a coating that essentially becomes part of the surface itself and forms a surface barrier.

Organosilanes are resilient once adhered to a surface and can resist harsh conditions such as ultraviolet radiation, water immersion, and high temperatures. It is also known that organosilanes have the ability to repel water and dirt.

There are presently several cleaning solutions used that contain organosilicon compounds, specifically, organosilanes. These cleaning solutions are typically used to remove odors, and are used as antibacterials, antifouling paints, general antimicrobials, disinfectants, and pesticides. The organosilane compositions are used in various industries: maritime, food, medical, waste, consumer goods, petroleum engineering, waterworks systems, construction materials, agriculture, and textiles for example.

Organosilane compositions are traditionally used in liquid form and applied to a surface. Organosilanes are lipophilic and can be difficult in forming homogenous liquids suitable for aqueous sprays, and they frequently require methanol as part of the compound or added to a solution to prevent degradation while stored. Shelf life and thermal degradation of organosilane solutions are a concern. Longevity, simplicity in manufacturing, and minimization of effects on non-intended organisms by organosilane compounds needs improvement.

SUMMARY

What is needed is a multi-purpose cleaning composition that has a long shelf life, is substantially permanent, does not leach once set or cured, has reduced tendency for thermal degradation, has a shelf life of at least one year, has minimal toxicity, and can be safely used in a variety of household, consumer, recreational, agricultural, medical, and industrial settings. The multi-purpose cleaning composition is also made simply by creating a liquor and then diluting the liquor with water while mechanically mixing.

Furthermore, what is needed is a multi-purpose cleaning composition comprising an organosilicon compound, such as an organosilane, stable in an aqueous solution or any other medium when stored and is stable after application to a substrate or surface. The composition is effective in reducing microbial adhesion, is effective at repelling pests, and is effective at reducing odors.

The composition comprises at least an organosilicon compound in an aqueous solution. Exemplary compositions can also include additives such as an ethoxylate compound, an alcohol, a sulfonate compound, a non-ionic detergent, and a solvent. The compositions may also include any one or a combination of cationic, zwitterionic, or amphoteric surfactants; wetting agents; dispersants; emulsifiers; detergents; foaming agents; saponins; capsaicinoids; volatilizing agents; coupling agents; hydrotropes; solublilizers; solvents; aromatic compounds; buffers; essential oils; fragrances; extended-release fragrances; dyes; pigments; enzymes; acids; hydrocarbons; waxes; gels; preservatives; repellants; chelating agents; antimicrobial compounds, and additional reagents and additives.

DETAILED DESCRIPTION

Introduction

The present disclosure provides generally for multi-purpose cleaning compositions and methods. The compositions described herein provide for multi-use compositions that may be stable in aqueous solutions, foams, powders, aerosols, micelles, epoxies, resins, emulsions, concentrates, cements, gels, lacquers, waxes, pastes, oils, extended-release media, or combinations thereof or any other medium.

The compositions may be used in the following applications and are not limited: reduction of transmission of invasive species; pesticide; biocide; antibacterial; biostatic; surface protectant; sealant; laminate; odor reducer; odor eliminator; deodorizer; antifouling; anti-biofouling; repellant; medical coating; antifungal; anticorrosive; prevention of biofilm formation; prevention of bio adhesion; prevention in pathogen transmission; mildewstat; anti-corrosive; preservative; sequestration solution; chelating solution; and antiviral.

The compositions may be used on natural or synthetic solid surfaces; applied to plants; applied to animals; mixed in with substrates; added to liquids, waxes, gels, creams, or pastes; sprayed in the air; applied to mixed waste; and used in industrial applications.

The compositions are safer, longer lasting, more stable, easier to apply to a surface, have reduced toxicity to non-targeted organisms, are more simple to make, and are able to repel pests and microbes. The exemplary compositions demonstrate improved and longer lasting odor reduction and odor elimination effects over traditional odor reduction compositions.

In the following sections, detailed descriptions of examples and methods of the disclosure will be given. The description of both preferred and alternative examples are exemplary only, and it is understood to those skilled in the art that variations, modifications, and alterations may be apparent. Therefore, the examples do not limit the breadth of the aspects of the underlying disclosure as defined by the claims.

Exemplary Compositions

Exemplary multi-purpose cleaning compositions include all derivatives, analogs, enantiomers, combinations, and mixtures of the ingredients described below. All molarities, forms of matter, proportions, percentages, weights, volumes, and ratios of each ingredient are implied.

The multi-purpose cleaning compositions may contain at least one active ingredient that has protectant, preservative, or biocidal properties. In some compositions, a multi-purpose cleaning composition may contain an organosilicon compound that exhibits protective, preservative, or biocidal properties. The organosilicon compound may be an organosilane, or more specifically an organosilicon quaternary ammonium compound. An example of a suitable organosilicon quaternary ammonium compound that can be used in the present invention has the following structure:

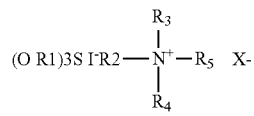

In the exemplary structure, R1 may be a hydrogen or an alkyl group with 1 to 8 carbons; R2 may be a hydrogen or an alkyl group with 1 to 8 carbons; R3 and R4 may be the same or different and may be selected from a group consisting of hydrogen and an alkyl group with 1 to 4 carbons; R5 may be a hydrogen or an alkyl group with 1 to 30 carbons; and X— may be a counterion moiety such as a sodium ion.

The silane moiety bonds covalently to a surface, allows for monomer crosslinking, and polymerizes with other molecules, and then becomes covalently unreactive with other molecules. The positively charged nitrogen attracts the negatively charged surface of microbes. The exemplary structure may have a long carbon chain that punctures cell walls and cell membranes of microbes that come in contact with an exemplary organosilane polymer. This prevents cellular adhesion to a polymer-coated surface, kills microbes, and prevents microbes from proliferating.

In some compositions, the organosilane has at least two different reactive functional groups. A reactive functional group may be an amino, epoxy, vinyl, methacrylate, or sulfur moiety for example. In some compositions, the organosilane may have non-reactive functional groups such as an alkyl moiety.

The organosilane moieties may be lipophilic or hydrophilic. In some compositions, the hydrolysable group may be an alkoxy, methoxy, ethoxy, isopropoxy, or acetoxy moiety that may couple or react with hydroxyl groups on or in the media such as a solid surface or mixed industrial waste and refuge to which the organosilane is applied.

The reaction with the hydroxyl groups creates the adhesion of the protective silane polymer to the medium and results in byproducts of alcohols such as ethanol or propanol or an acid such as acetic acid.

It has previously been shown that quaternary ammonium organosilane polymers, can form clear solutions in aqueous media such as deionized water which are stable over extended periods of time without the use of emulsion technology involving the application of high shear forces by further including a water soluble organic, non-silicon quaternary ammonium compound along with nonionic, amphoteric, sarcosine anionic or certain cationic surfactants. The exemplary compositions had been shown to resist thermal breakdown when stored for at least one year in temperatures of up to 37 degrees Celsius.

A composition may be a water based alkaline, acidic, or pH-neutral product that may contain solvents, surfactants, chelating agents, antimicrobial agents and/or other materials such as fragrances and dyes. In some compositions, a combination of solvents, chelating agents, and antimicrobial agents in an aqueous solution may produce a clear, stable composition with no precipitants and no need for aftermarket mixing. In some compositions, a composition may be stable in its concentrated liquor form and readily mix with a solvent such as water. In some compositions, the solvent may be a glycol ether or low molecular weight alcohol, the surfactant may be a non-ionic surfactant, the chelating agent may be a nitriloacetate, and the antibacterial, biocidal, protective, repellant, or odor-reducing agent may be a silicon-containing quaternary ammonium salt. In some compositions, a chelating agent may be absent.

Some compositions may comprise alcohol solvents such as ethanol, methanol, butanol, or propanol either as an additive or as a byproduct in trace amounts of less than 1 percent from the organosilane in aqueous solution. In some aqueous compositions in spray or aerosol form for example, reagents such as ethane may be added to increase the volatility of the composition and reduce drying or curing time.

In some compositions, the antimicrobial, surface protectant, biocide, or odor eliminator is a quaternary ammonium functional organosilane containing hydrolyzable groups. For example, in a composition, the antimicrobial agent may be 3-(trimethoxysilyl) propyl octadecyl dimethyl ammonium chloride or 3-(trihydroxysilyl) propyl methylphosphonate monosodium. Other examples of organosilicon or organosilane compounds that may be suitable for use include, but are not limited to, (3-N, N-dimethyl-3-N-n-octylammoniopropyl) trimethoxysilane chloride, 3(trihydroxysilyl) propyldimethyl octadecyl ammonium chloride, (3-N,N,N-triethanolammoniopropyl) trimethoxysilane chloride, (3-glycidoxypropyl) diethoxysilane, or (3-N,N-dimethyl-3-N-n-hexadecylammoniopropyl) trimethoxysilane chloride.

A non-ionic surfactant or detergent may be an alkyl, aryl polyethylene glycol ether, ethylene glycol, or any version of an ethylene oxide chain containing a water soluble portion. A surfactant, coupling agent, hydrotrope, solubilizer, or solvent may be a sulfonate such as a hydroxy sulfonate, xylene sulfonate, arylalkyl sulfonate, or olefin sulfonate and their related salts and variations. In some compositions, simple lye soap may be used as the surfactant.

These surfactants are present to lower the surface tension of the water and to provide improved wetting and detergency. The non-ionic surfactant preferably has a hydrophilic-lipophilic balance number of 18.0 or less and may raise the pH of the composition.

Some compositions may contain a non-ionic surfactant having an ethoxylate moiety such as nonylphenol ethoxylates, octylphenol ethoxylates, alkyl ethoxylates, ethoxylated amine salts, alkylphenol ethoxylates, and other derivatives, and mixtures thereof. In some compositions, alkylphenol ethoxylates are preferred to nonylphenol ethoxylates because alkylphenol ethoxylates have been found to cause less teratogenic effects than nonlyphenol ethoxylates. Some compositions may contain oxylates such as oxyethylated fatty alkyl phenols or alkylethoxylated alcohols to function as an emulsifier to aid in forming a miscible mixture of the lipophilic organosilane in an aqueous solution and may include foam stabilizing agents such as silicon-containing polyethers.

In compositions mixed in a wax or lipophilic or anhydrous medium, surfactants may not be required or may be reduced because organosilanes are lipophilic and will homogenize in a lipophilic medium. In such compositions, water may need to be applied separately to a substrate or medium either before or after application of the composition in a lipophilic medium, so the hydrolysis and condensation reactions of the organosilane can take place for proper adhesion to the substrate or medium.

In some compositions, fragrances may be added to enhance or complement odor elimination or reduction. Essential oils such as citrus or cedar oils may be added to enhance or complement antibacterial, protectant, odor-reducing, antifouling, or biocidal properties. Fragrances may be any one or a combination of esters, linear terpenes, cyclic terpenes, aromatics (benzenes), amines, alcohols, aldehydes, ketones, lactones, or thiols.

Exemplary esters may be methyl butyrate, methyl anthranilate, isoamyl acetate, octyl acetate, benzyl acetate, or geranyl acetate. Exemplary linear terpenes may be geraniol, citral, citronellol, linalool, or nerolidol. Exemplary cyclic terpenes may be eucalyptol, carvone, camphor, or limonene. Exemplary aromatics may be cinnamaldehyde, vanillin, or benzaldehyde. Exemplary amines may be indole, pyridine, or skatol. Exemplary alcohols may be furaneol or menthol. Exemplary aldehydes may be acetaldehyde, hexyl cinnamaldehyde, hexanal, or anisic aldehyde. Exemplary esters may be fructone or ethyl methylphenylglycidate. Exemplary ketones may be dihydrojasmone. Exemplary lactones may be gamma decalactone, massoia lactone, or gamma nonalactone. Exemplary thiols may be grapefruit mercaptan.

In some compositions, additional pesticides, biocides, antifouling agents, and/or repellants may be added but are not required.

Exemplary Methods of Making Compositions

Compositions may be made in large-scale industrial quantities or in small-scale batches and stored for months or years up to 37 degrees Celsius. The exemplary compositions do not require complex mixing processes such as required modifications of temperature and pressure. A liquor may simply be mechanically mixed with a solvent such as water to dilute to a desired concentration. Mechanical mixing may be done in vats with manual or automatic stirring. A liquor or a liquor diluted in an aqueous solution may be decanted and stored in closed plastic containers such as spray bottles for household use or totes having hundreds of gallons of capacity.

In some method steps, a composition may be made by mixing the constituents to allow for a complete and homogenous composition without the need for extra homogenization steps. In some method steps, a chelating agent, a buffer or a pH modifier may be mixed with a solvent, then an antimicrobial, cleaning, repellant, or protectant agent added, and then inert ingredients or additives such as dyes, fragrances, or essential oils may be added.

In some method steps, an additional antifouling, virucidal, biocidal or repellant may be added such as a citranellol, capsaicinoid, 3-[N-butyl-N-acetyl]-aminopropionic acid, ethyl ester, para-menthane-3,8-diol, 2-(2-hydroxyethyl)-1-piperidinecarboxylic acid 1-methylpropyl ester, N,N-diethyl-m-toluamide, N,N-diethyl-3-methyl-benzamide.

Additives and complementary and enhancing ingredients such as additional dyes, pigments, fragrances, aromatic compounds, and essential oils such as tea tree oil, peppermint oil, lemon oil, or eucalyptus oil may be added along with additional solvents and agents to increase volatility, thus decreasing dry time.

Exemplary formulae based on possible combinations are included. A liquor may be made with a combination of at least an aqueous organosilane. The liquor may be diluted with water in various ratios such as a 1:10 ratio, 2:10 ratio, 1:20 ratio, or 2:20 ratio, or any in between or as described in the examples below. A liquor may also comprise a surfactant or an additive. A liquor may also comprise a fragrance compound. In some compositions, an organosilane may be present in a range of approximately 0.01 to approximately 10 percent by volume in a composition. Exemplary compositions may contain an aqueous organosilane at 0.08 percent, 1.1 percent, 1.2 percent, 1.4 percent, 2 percent, 3 percent, 4 percent, and 5 percent. A liquor may comprise a composition by up to 90% but as low at 1%.

Exemplary Applications and Methods of Use

Some compositions may be in various media and in various forms such as an aerosol, liquid, powder, wax, cream, paste, epoxy, cement, glaze, lacquer, paint, or coating.

Compositions may be applied to any organic, inorganic, natural, or synthetic medium. Media may be plants, animals, waste, refuse, household goods, buildings, tools, medical and laboratory instruments, textiles, personal care items, industrial machinery, recreational items (such as toys, games, SCUBA gear, watersports gear, amusement park rides, arcades, and surfboards and the like), motorized and non-motorized water vessels, vehicles, trains, aircraft, and any other item or location.

In some methods, a composition may be sprayed manually or automatically into the air or onto a surface or medium. The composition may be allowed to set, cure, or bond for a period of time sufficient to allow for polymerization and coupling to take place. Excess composition applied to the surface may be wiped away or left to remain and air dry.

In some methods, the composition may be applied to a dry or wet surface. The composition may be applied by methods other than spraying: coating, painting, brushing, spackling, pouring, or rubbing. In some methods, a composition is provided in a spray or mist bottle and sprayed from a distance of 3 to 7 feet or a distance of 4 to 6 feet away or from 1 to 3 meters away from a target area. The spray or mist contacts a surface and bonds to the surface, whether the surface is wet, dry, solid, or non-solid such as carpet or fabric. In approximately 15-25 minutes, but usually within about 20 minutes, the spray or mist will have dried or evaporated. In some methods, the composition may be applied to the interior and exterior of a water vessel to prevent adhesion, fouling, corrosion, and transmission of invasive species.

In some methods, a composition may be sprayed in interior and exterior trash and waste areas such as trash compactors, dumpsters, industrial trash processing rooms, and landfills. Application of a composition results in a drastic decrease in the detection of odors within approximately 20 minutes.

In one household example, a multi-purpose cleaning composition comprises approximately 1% by volume of an organosilane, approximately 3% by volume of surfactants, approximately 3% by volume of aqueous fragrance, approximately 3% by volume of additives, and approximately 90% by volume of water. The organosilane, surfactants, fragrance, and additives make up a liquor. In an alternative composition, additives are not present. The liquor is diluted with water and mechanically mixed. The resulting composition may have a pH in the range of 6 to 8. The resulting multi-purpose cleaning composition is provided in spray bottles of one liter or less for household consumer use. A person sprays the contents for example in a compost bin with enough composition to cover the top layer of the compost. Within 20 minutes, bad odors will not be detected. The odor reduction or elimination is effective for at least 5 days without requiring additional application and without disrupting the composting process.

In another household example, a multi-purpose cleaning composition comprises 0.05% by volume of an organosilane, approximately 1% by volume of surfactants, approximately 1% by volume of additives, approximately 1% by volume of aqueous fragrance, and approximately 96.5% by volume of water. This exemplary composition may be provided in spray bottles 1 liter or smaller for household consumer use. A person sprays the contents onto carpet or flooring to remove or reduce odors. The carpet may be left to dry on its own or may be vacuumed after at least 15 minutes. The odor reduction or elimination is effective for at least 20 days without requiring additional application.

In one industrial example, a multi-purpose cleaning composition comprises 3% by volume of an organosilane, approximately 2% by volume of surfactants, approximately 4% by volume of additives, approximately 1% by volume of aqueous fragrance, and approximately 90% by volume of water. The exemplary solution is applied to a surface in an area frequented by rodents such a construction site, buildings, and vehicles where items such as electrical wires, insulation, drywall, and pipes are targeted by pests such as rodents. Rodents are known to hide in large commercial vehicles, attics, and basements and chew through the wiring, pipes, insulation, and drywall as well as cause an odor from droppings and urine. A person sprays the exemplary composition throughout the area and directly on the targeted wiring, pipes, insulation, or drywall. The spray is left to dry on its own, or remaining liquid may be wiped off after approximately 20 minutes. The composition significantly reduced odor and repelled rodents for a minimum of 20 days and prevented further damage by the rodents.

In another industrial example, a multi-purpose cleaning composition comprises 5% by volume of an organosilane, approximately 3% by volume of surfactants, approximately 2% by volume of additives, approximately 5% by volume of aqueous fragrance, and approximately 85% by volume of water. The exemplary composition is sprayed with a misting system intermittently in mixed solid waste processing plants, dumpsters, and landfills. The intermittent spray can be conducted at intervals of four times a day, three times a day, twice a day, once a day, every other day, or once a week depending on the severity of the odor. A misting system may be manually or automatically discharged to expel a mist, aerosol, or spray of an exemplary composition. Within 20 minutes odor is significantly reduced.

For example, in one trial, an olfactometer was used to evaluate the severity of odor from a landfill within a one-mile radius. After 20 minutes of application of an exemplary cleaning composition, the olfactometer was used again. Sulfurous, cresol, indole, and mercaptan odors characteristic of landfills, municipal solid waste, and sewer sludge were not detected. It was also observed, that at dumpsters, an exemplary cleaning composition did not kill bees or birds, indicating that exemplary compositions were effective for long-lasting and significant odor reduction while not harming non targeted life.

CONCLUSION

The foregoing is a description of exemplary multi-purpose cleaning compositions and methods. However, it is to be understood that the present disclosure is not limited to the particular descriptions disclosed. The present disclosure also comprises any modifications or equivalents within the scope of the claims.

What is claimed is:

1. A multi-purpose cleaning composition, the cleaning composition comprising an aqueous mixture of:
   a) an organosilane with hydrolyzable groups selected from the group consisting of:
      i) 3-(trimethoxysilyl) propyl octadecyl dimethyl ammonium chloride,
      ii) 3-(trihydroxysilyl) propyl methylphosphonate monosodium, (3-N,N-dimethyl-3-N-n-octylammoniopropyl) trimethoxysilane chloride,
      iii) 3-(trihydroxysilyl) propyldimethyl octadecyl ammonium chloride,
      iv) (3-N,N,N-triethanolammoniopropyl) trimethoxysilane chloride,
      v) (3-glycidoxypropyl) diethoxysilane, (3-N,N-dimethyl-3-N-n-hexadecylammoniopropyl) trimethoxysilane chloride, and combinations thereof;
   b) a surfactant;
   c) a fragrance; and
   d) water.

2. The composition of claim 1 wherein the surfactant is selected from the group consisting of lye soap, polyethylene glycol ether, hydroxy sulfonate, xylene sulfonate, arylalkyl sulfonate, olefin sulfonate, nonylphenol ethoxylate, octylphenol ethoxylate, alkyl ethoxylate, ethoxylated amine salts, alkylphenol ethoxylate, and combinations thereof, wherein the composition may further comprise ethylene glycol.

3. The composition of claim 1 wherein the fragrance is selected from the group consisting of esters, linear terpenes, cyclic terpenes, aromatics, amines, alcohols, aldehydes, ketones, lactones, or thiols and combinations thereof.

4. The composition of claim 1 further comprising an additive.

5. The composition of claim 4 wherein the additive is selected from the group consisting of citranellol, capsaicinoid, 3-[N-butyl-N-acetyl]-aminopropionic acid, ethyl ester, para-menthane-3,8-diol, 2-(2-hydroxyethyl)-1-piperidinecarboxylic acid 1-methylpropyl ester, N,N-diethyl-m-toluamide, N,N-diethyl-3-methyl-benzamide, tea tree oil, lemon oil, eucalyptus oil, capsaicinoids, and combinations thereof.

6. The composition of claim 1 wherein the organosilane is present at approximately 1% volume, the surfactant is present at approximately 3% volume, the fragrance is present at approximately 3% volume, and the water is present at approximately 93% volume.

7. The composition of claim 4 wherein the organosilane is present at approximately 0.05% volume, the surfactant is present at approximately 1% volume, the additive is present at approximately 1% volume, the fragrance is present at approximately 1% volume, and the water is present at approximately 96.5% volume.

8. The composition of claim 4 wherein the organosilane is present at approximately 3% volume, the surfactant is present at approximately 2% volume, the additive is present at approximately 4% volume, the fragrance is present at approximately 1% volume, and the water is present at approximately 90% volume.

9. The composition of claim 4 wherein the organosilane is present at approximately 5% volume, the surfactant is present at approximately 3% volume, the additive is present at approximately 2% volume, the fragrance is present at approximately 5% volume, and the water is present at approximately 85% volume.

10. A method of applying the composition of claim 6 to reduce odor from a compost bin and its compost, the method comprising the steps:
    spraying the compost bin compost from a distance of approximately 1 to 3 meters;
    allowing the composition to cure for approximately 15 to 25 minutes; and
    re-applying the composition in approximately 7 days.

11. A method of applying the composition of claim 7 to reduce odor from a non-solid surface such as fabric or carpet, the method comprising the steps:
    spraying the non-solid surface from a distance of approximately 1 to 3 meters allowing the composition to cure for approximately 15 to 25 minutes; and
    re-applying the composition in approximately 14 days.

12. A method of applying the composition of claim 8 to reduce odor from spaces frequented by rodents and repelling the rodents, the method comprising the steps:
    spraying the spaces frequented by rodents, including items such as pipes, wires, drywall, and insulation, from a distance of approximately 1 to 3 meters;
    allowing the composition to cure for approximately 15 to 25 minutes; and
    re-applying the composition in approximately 20 days.

13. A method of applying the composition of claim 9 to reduce odor from municipal waste such as sewer sludge and trash, the method steps comprising:
    connecting a container of the composition to a spray or mist system at a source of municipal waste such as trash and sludge in a processing room or a landfill;
    intermittently spraying the source of municipal waste at intervals of either four times a day, three times a day, twice a day, once a day, every other day, or once a week;
    allowing the composition to cure for approximately 20 minutes; and
    re-applying the composition at an interval of either four times a day, three times a day, twice a day, once a day, every other day, or once a week.

14. A method of providing the composition of claim 1, the method steps comprising:
    creating a liquor by combining an organosilane, a surfactant, and fragrance;
    diluting the liquor with water at a 1 to 10 ratio;
    stirring mechanically the mixture for 10 minutes;
    decanting the mixture into a plastic container;
    closing the plastic container; and
    storing the mixture in the plastic container until needed.

15. A method of providing the composition of claim 4 the method steps comprising:
   creating a liquor by combining an organosilane, a surfactant, a fragrance, and an additive;
   diluting the liquor with water at a 1 to 10 ratio;
   stirring mechanically the mixture for 10 minutes;
   decanting the mixture into a plastic container;
   closing the plastic container; and
   storing the mixture in the plastic container until needed.

16. The composition of claim 1 whereby the composition has a pH from approximately 6 to approximately 8.

17. The composition of claim 4 whereby the composition has a pH from approximately 6 to approximately 8.

18. The composition of claim 1 whereby the shelf life is greater than 1 year when stored in a closed plastic container at a temperature of 37 degrees Celsius.

19. The composition of claim 4 whereby the shelf life is greater than 1 year when stored in a closed plastic container at a temperature of 37 degrees Celsius.

* * * * *